United States Patent
Chao et al.

(10) Patent No.: US 9,623,137 B2
(45) Date of Patent: Apr. 18, 2017

(54) ESSENTIAL OIL DIFFUSER

(71) Applicants: Hsuan-Yu Chao, Taipei (TW); Mei-Mei Tsai, Taipei (TW)

(72) Inventors: Hsuan-Yu Chao, Taipei (TW); Mei-Mei Tsai, Taipei (TW)

(*) Notice: Subject to any disclaimer, the term of this patent is extended or adjusted under 35 U.S.C. 154(b) by 5 days.

(21) Appl. No.: 14/876,338

(22) Filed: Oct. 6, 2015

(65) Prior Publication Data

US 2016/0107186 A1 Apr. 21, 2016

(30) Foreign Application Priority Data

Oct. 16, 2014 (CN) .................... 2014 2 0599068 U

(51) Int. Cl.
| | | |
|---|---|---|
| *B05B 17/06* | (2006.01) | |
| *A61L 9/14* | (2006.01) | |
| *A61M 11/00* | (2006.01) | |
| *A61L 9/00* | (2006.01) | |
| A61M 21/00 | (2006.01) | |

(52) U.S. Cl.
CPC ........ *A61L 9/14* (2013.01); *A61L 9/00* (2013.01); *A61M 11/005* (2013.01); *A61M 2021/0016* (2013.01); *A61M 2205/8262* (2013.01); *B05B 17/0684* (2013.01)

(58) Field of Classification Search
CPC .................... B05B 17/0607; B05B 17/0646
USPC ...... 239/102.1, 102.2, 4, 326; 392/386, 390, 392/394–396
See application file for complete search history.

(56) References Cited

U.S. PATENT DOCUMENTS

| 5,967,807 | A * | 10/1999 | Wu ........................ H01R 29/00 439/131 |
| --- | --- | --- | --- |
| 6,361,752 | B1 * | 3/2002 | Demarest ................ A61L 9/037 165/104.26 |
| 7,462,329 | B2 * | 12/2008 | Wefler ....................... A61L 9/12 422/124 |
| 7,793,860 | B2 * | 9/2010 | Bankers .............. A01M 1/2044 206/223 |
| 7,891,580 | B2 * | 2/2011 | Valpey, III .......... B05B 17/0646 128/200.16 |
| 2013/0126637 | A1 * | 5/2013 | Hsieh ................... A61M 11/005 239/102.2 |

FOREIGN PATENT DOCUMENTS

| CN | 204293562 U | 4/2015 |
| --- | --- | --- |
| TW | M482442 U | 7/2014 |
| TW | M482447 U | 7/2014 |

* cited by examiner

*Primary Examiner* — Arthur O Hall
*Assistant Examiner* — Tuongminh Pham
(74) *Attorney, Agent, or Firm* — Chun-Ming Shih

(57) ABSTRACT

An essential oil diffuser comprises a main body and a power plug. The main body includes a shell, an electric circuit board, a connector shell, and an ultrasonic vibration module. Wherein, a receiving room is formed in the shell, an opening is formed at one end of the shell, and a shell hole is disposed on an upper shell. The connector shell is provided in the receiving room on a side of the shell opening. A receiving room is also formed in the connector shell, to receive an essence container screwed therein. The ultrasonic vibration module is disposed in the receiving room of the connector shell, and it is provided with an atomized liquid outlet corresponding to the shell hole and the connector hole, and is sleeved in the connector shell by means of a sleeve piece.

7 Claims, 7 Drawing Sheets

ESSENTIAL OIL DIFFUSER

BACKGROUND OF THE INVENTION

Field of the Invention

The present invention relates to a diffuser, and in particular to an essential oil diffuser, that is connected to a power supply through a power plug, to obtain the power required to activate an ultrasonic vibration module in the main body, to atomize the essence in an essence container, and then output the atomized essence from the essential oil diffuser to the surroundings.

The Prior Arts

In recent years, due to the rapid progress and development of the medical science and cosmetics industry, people are able to pay more attention to their health, medical cares, and appearances. Usually, for essence therapy, plant essential oil is used. In application, an electrical heating essence device, an electrical pumping and atomizing device, or an ultrasonic atomizing device is utilized to atomize the liquid essential oil, and then eject and spray it into the air, to be absorbed by human body readily.

For the conventional electrical heating essence device, an electrical heating element contained therein is used to heat the essential oil liquid continuously, and after heating it to a certain degree, the fragrance of the essence are diffused in the surroundings.

For the conventional electrical pumping and atomizing device, an electrical pump motor is used, to transport air to the ejection tube in a container. Then, the ejection tube or even an electrical fan is used to make the air flow, and to spray the essential oil into mist, so that its surroundings are full of the fragrance of the essential oil. The structure and design of the ejection tube can be different for various manufacturers, yet its function is to make the air flow through to atomize the liquid essence into mist. For details of the conventional electrical pumping and atomizing device, refer to Taiwan Patent No. M482442 "Liquid Nebulizing Apparatus".

The conventional electrical appliances making use of the ultrasonic atomizing principle includes: ultrasonic aroma diffuser, beauty/health care device, air essence device, ultrasonic cleaning device, and air cleaning device, that are utilized extensively in beauty shops and ordinary households. Presently, the device utilizing ultrasonic atomizing principle is designed with a container in its shell to receive liquid, and a vibrator is provided to generate high frequency vibrations, to vibrate the liquid stored in the container, thus atomizing the liquid into minute particles of mist, and diffusing it into the surroundings. In this respect, to the deteriorating environment of the urban community, ultrasonic aroma diffuser, beauty/health care device, air essence device, ultrasonic cleaning device, and air cleaning device having ultrasonic atomizing capability, may have beneficial effects on the environment. For the details of the structure and design of the conventional ultrasonic atomizing device, refer to Taiwan Patent No. M482447 "Ultrasonic Focusing and Energy Saving Atomizing Device".

However, the disadvantages of the Prior Art is that, in applying the existing essential oil diffuser, for the essence container presently available on the market, its essence liquid contained therein must be reloaded into a specific container to be applicable, thus the essence container can not be used directly by the conventional essential oil diffuser.

Therefore, presently, the design and performance of the essential oil diffusing device are not quite satisfactory, and it leaves much room for improvement.

SUMMARY OF THE INVENTION

In view of the problems and drawbacks of the prior art, the present invention provides an essential oil diffuser, to overcome the shortcomings of the prior art.

A major objective of the present invention is to provide an essential oil diffuser, including a main body and a power plug. Wherein, the main body includes a shell, a switch, an electric circuit board, a connector shell, an opening, an ultrasonic vibration module, and a pivot slot. The shell is composed of an upper shell and a lower shell, while a receiving room is formed in the shell. One end of the shell is formed into an opening, while the upper shell is provided with a shell hole. The switch is connected electrically to the electric circuit board. The electric circuit board is disposed in the receiving room of the shell, and is connected electrically to the ultrasonic vibration module. The connector shell is disposed in the receiving room on the side of the shell hole, while the ultrasonic vibration module is disposed inside the connector shell. The essence container can be screwed into the connector shell, with its sleeve piece covering the opening of the essence container. The ultrasonic vibration module is provided with an atomized liquid outlet corresponding to the shell hole and a connector hole, and is connected electrically to the electric circuit board. The power plug is pivotally disposed at other end of the main body, and is connected electrically to the electric circuit board. In this approach, the essence (essential oil) in the essence container is atomized by the vibrations generated by the ultrasonic vibration module, to be ejected and sprayed out from the atomized liquid outlet.

Also, in the present invention, an aroma rod presently available on the market can be inserted behind the essence container, to absorb the essence by means of the siphon principle. In addition, the aroma rod can be inserted into the through-hole on a side of the cover of the sleeve piece, and is in communication with the absorbent in the through-hole on a side of the hollow slot, the atomized liquid outlet of the ultrasonic vibration module, and the connector hole of a first shell. The aroma rod is made of cotton rod or cotton strip. As such, the essence can be given out smoothly.

When the power plug is inserted into the insertion slot of a power socket, the main body still can be rotated relative to the power plug for 180 degrees, to adjust the main body to a suitable position to operate. As such, the atomized liquid outlet is positioned properly, and the switch can be turned on. The switch is connected electrically to the electric circuit board, such that power is transmitted to the ultrasonic vibration module from the power plug through the electric circuit board. Then, the ultrasonic vibration module generates vibrations to atomize the essence molecules, to be ejected out of the essential oil diffuser to dissipate in the surrounding area.

The disadvantages of the Prior Art is that, in applying the existing essential oil diffuser, for the essence container presently available on the market, its liquid essence contained therein must be reloaded into another container to be applicable, thus the essence container can not be used directly by the conventional essential oil diffuser. However, in the present invention, the essence container can be screwed into the connector shell of the main body, so that the liquid essence in the essence container can be used directly, without the need to purchase another container or to perform reloading.

Further, usually, the air molecules in the essence container tend to act on the essence molecules, and bring them to dissipate in the essence container, and thus being volatile.

Therefore, after the essence container is screwed into the connector shell, the air molecules and essence molecules dissipated in the essence container, due to the vibrations of the ultrasonic vibration module, they will pass through the through hole on the side of the hollow slot of the sleeve piece, the atomized liquid outlet of the ultrasonic vibration module, and the connector hole of the first shell, to be ejected and sprayed out of the essential oil diffuser.

Moreover, an aroma rod (cotton rod or cotton strip) currently available on the market can be inserted onto the essence container, to absorb the essential oil by means of the siphon principle, so that the aroma rod can be full of essential oil to be volatile. Also, the aroma rod is inserted onto the through hole at the side of cover of the sleeve piece, such that when the ultrasonic vibration module generates ultrasonic vibrations, the air molecules and essence molecules in the essence container are atomized, and then are ejected out of the essential oil diffuser, in achieving smooth spraying of essence and fragrance into the surrounding areas.

Further scope of the applicability of the present invention will become apparent from the detailed descriptions given hereinafter. However, it should be understood that the detailed descriptions and specific examples, while indicating preferred embodiments of the present invention, are given by way of illustration only, since various changes and modifications within the spirit and scope of the present invention will become apparent to those skilled in the art from this detailed descriptions.

BRIEF DESCRIPTION OF THE DRAWINGS

The related drawings in connection with the detailed descriptions of the present invention to be made later are described briefly as follows, in which.

DETAILED DESCRIPTION OF THE PREFERRED EMBODIMENT

Figure 1:
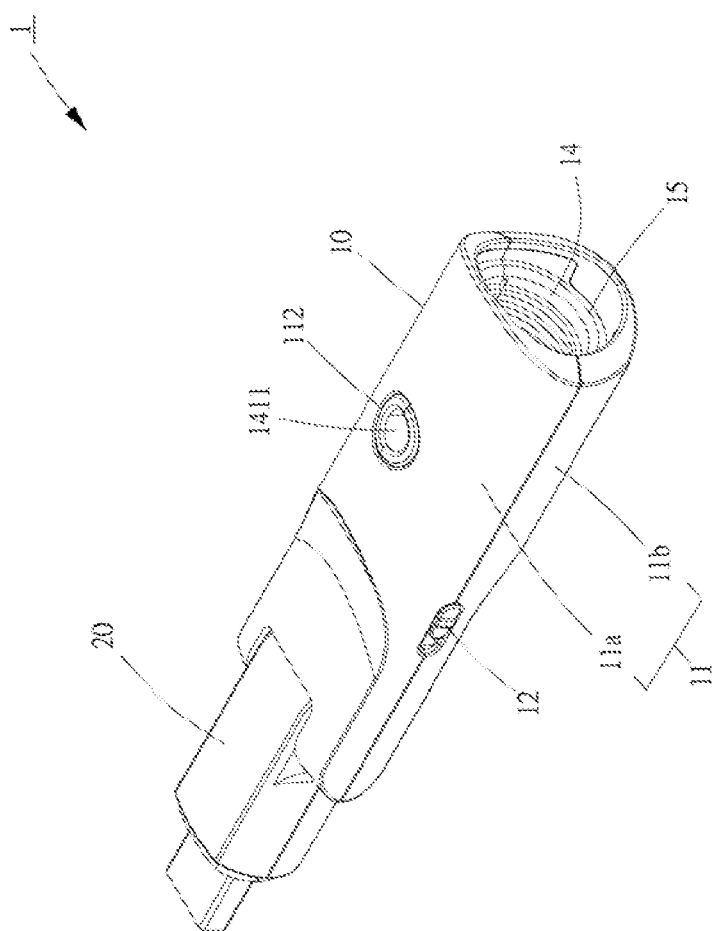
FIG. 1 is a schematic diagram of outer appearance of an essential oil diffuser according to an embodiment of the present invention.
Figure 2:
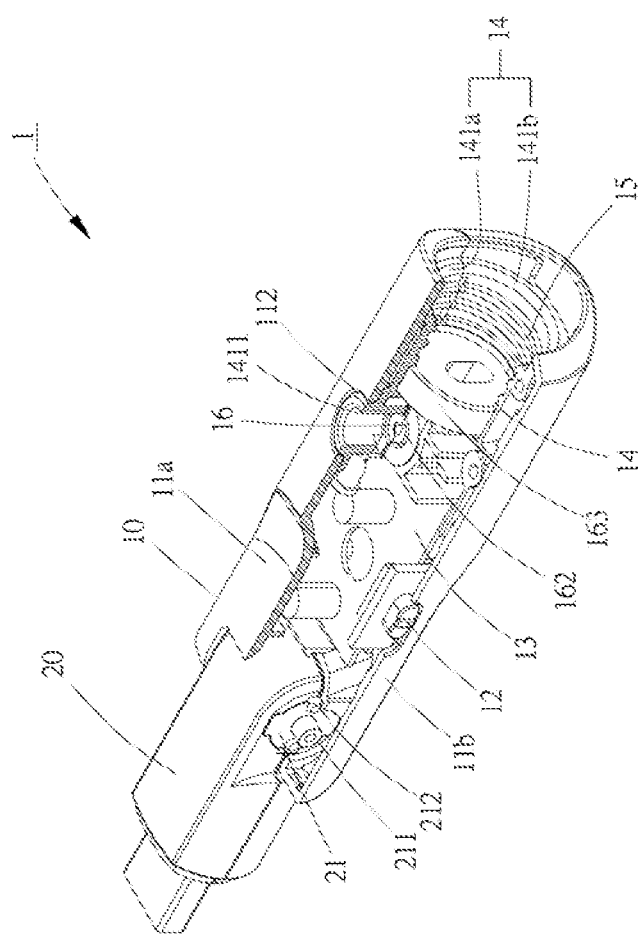
FIG. 2 is a cross section view of an essential oil diffuser according to an embodiment of the present invention.
Figure 3:
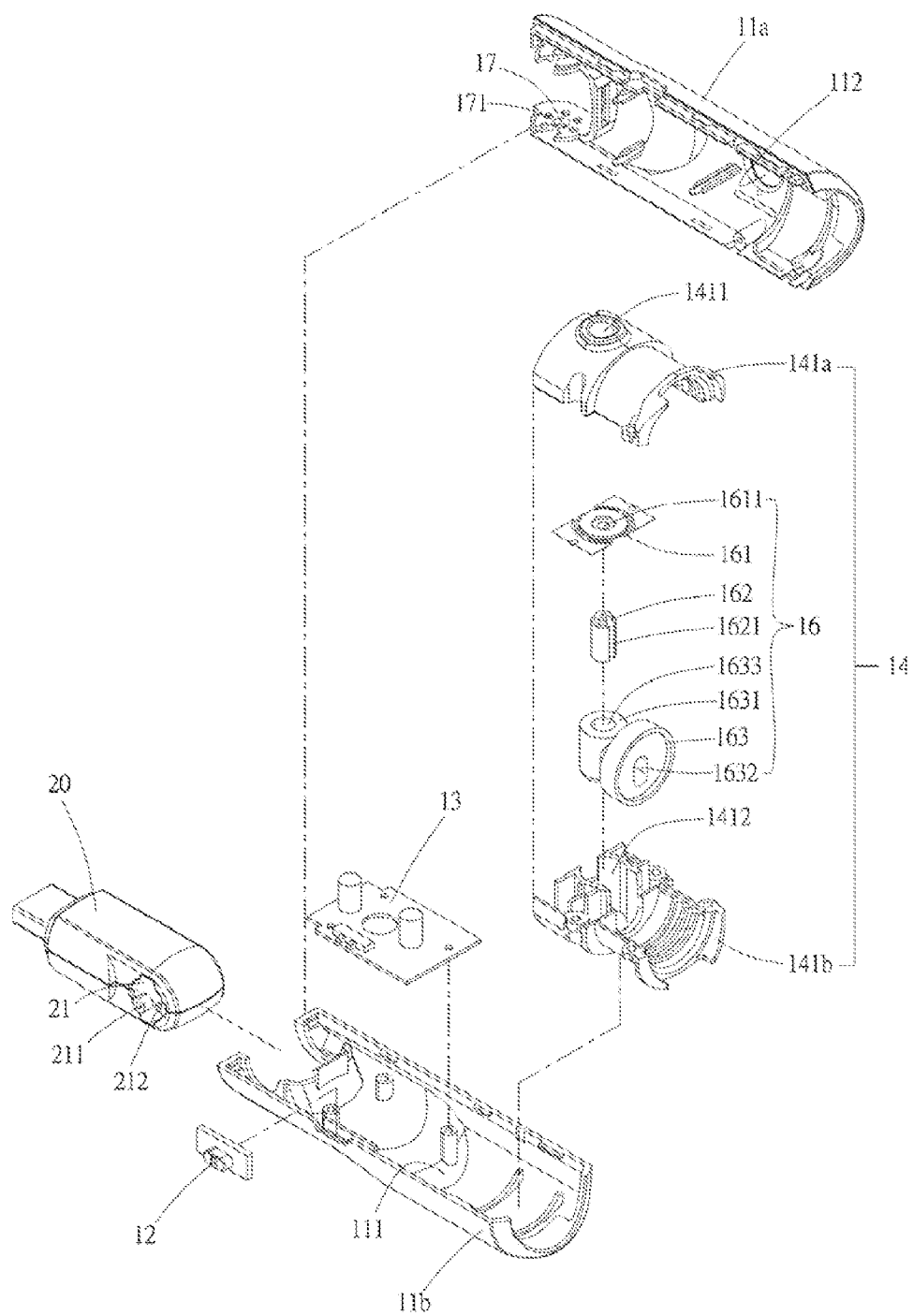
FIG. 3 is an exploded view of an essential oil diffuser according to an embodiment of the present invention.
Figure 4:
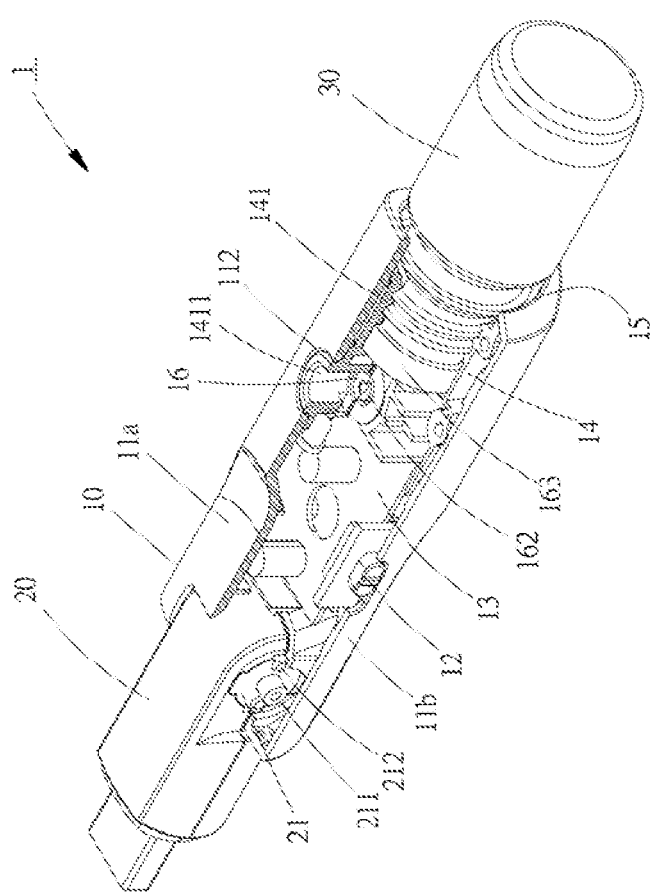
FIG. 4 is a cross section view of an essential oil diffuser in usage according to an embodiment of the present invention.

The purpose, construction, features, functions and advantages of the present invention can be appreciated and understood more thoroughly through the following detailed description with reference to the attached drawings.

Refer to FIGS. 1 to 4 respectively for a schematic diagram of outer appearance of an essential oil diffuser according to an embodiment of the present invention; a cross section view of an essential oil diffuser according to an embodiment of the present invention; an exploded view of an essential oil diffuser according to an embodiment of the present invention; and a cross section view of an essential oil diffuser in usage according to an embodiment of the present invention.

As shown in FIGS. 1 to 4, the essential oil diffuser 1 is formed by a main body 10, and a power plug 20. The main body 10 includes a shell 11, a switch 12, an electric circuit board 13, a connector shell 14, an opening 15, an ultrasonic vibration module 16, and a pivot slot 17. The shell 11 is composed of an upper shell 11a and a lower shell 11b, while in the shell 11 is formed a receiving room 111. One end of the shell 11 is formed into an opening 15, while in the upper shell 11a is provided with a shell hole 112. The switch 12 is connected electrically to the electric circuit board 13. The electric circuit board 13 is disposed in the receiving room 111 of the shell 11, and is connected electrically to the ultrasonic vibration module 16. The connector shell 14 is disposed in the receiving room 111 on the side of the shell opening 15, while inside the connector shell 14 is also formed a receiving room 1412. The connector shell 14 is provided with a connector hole 1411 corresponding to the shell hole 112.

Figure 5:
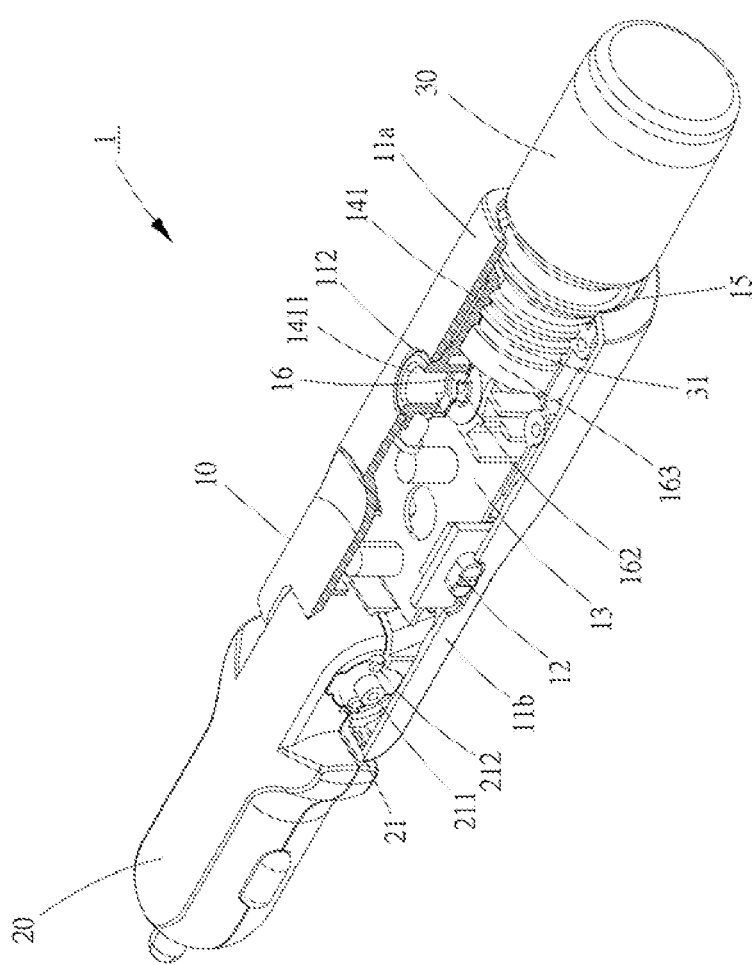
FIG. 5 is a cross section view of another essential oil diffuser according to another embodiment of the present invention.
Figure 6:
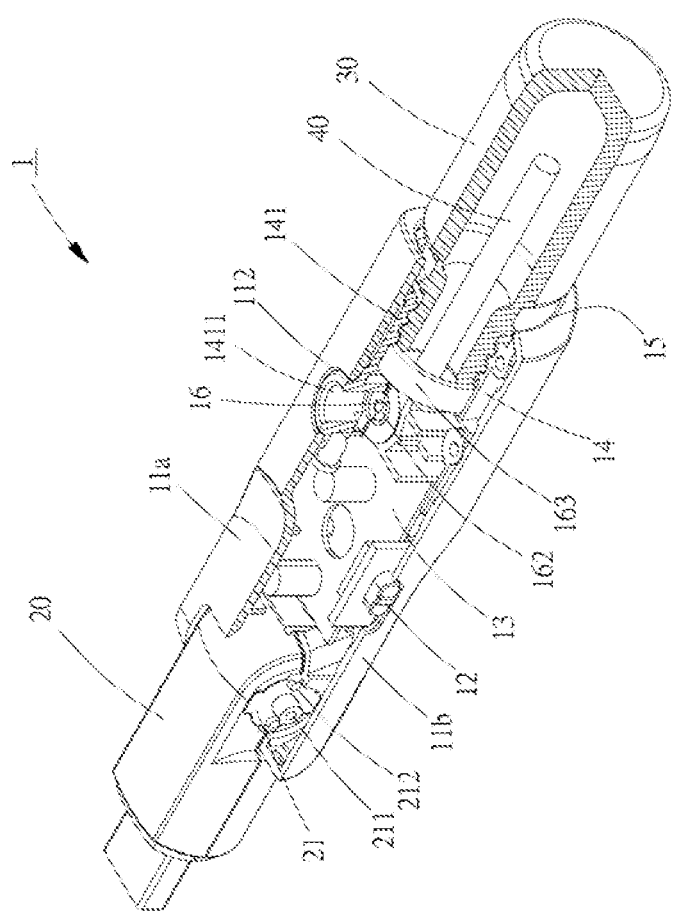
FIG. 6 is a cross section view of a further essential oil diffuser according to a further embodiment of the present invention.

The essence container 30 can be screwed into the connector shell 14 (refer to FIGS. 4, 5, 6, 7A, and 7B), that is able to cover the opening 31 of the essence container 30. The ultrasonic vibration module 16 is placed into the receiving room 1412 of the connector shell 14. The ultrasonic vibration module 16 is provided with an atomized liquid outlet 1611 corresponding to the connector hole 1411, and is connected to the connector shell 14. The ultrasonic vibration module 16 includes an ultrasonic vibrator 161, an absorbent 162, and a sleeve piece 163. The ultrasonic vibrator 161 is sleeved inside the connector shell 14 by means of the sleeve piece 163, and is connected electrically to electric circuit board 13. The sleeve piece 163 is provided with a hollow slot 1631, with its one side extended a cover 1632, and a through hole 1633 provided therein, and is connected and in communication with the hollow slot 1631 and the cover 1632. The center of the absorbent 162 is provided with an axial hole or a slot 1621, while the absorbent 162 is a high absorption cotton column, with its center provided with a siphon tube (not shown). The absorbent 162 is sleeved into the through hole 1633 at one end of the hollow slot 1631, while the aroma rod 40 is sleeved around by the cover 1632 at its one end (as shown in FIG. 6). On the two inner sides at the other end of the main body 10 are each provided with a pivot slot 17, and more than one slot port 171.

The connector shell 14 is provided with a first shell 141a and a second shell 141b, that can be fitted together to form a shell 141. The first shell 141a is provided with a connector hole 1411 corresponding to the atomized liquid outlet 1611 of the ultrasonic vibration module 16. A receiving room 1412 of the connector shell 14 is provided inside the second shell 141b. After the first shell 141a and the second shell 141b of the connector shell 14 are fitted together, the essence container 30 can be screwed therein, and the cover 1632 of the sleeve piece 163 is used to cover the opening 31 of the essence container 30, to form tight seal against water. As such, this makes the essence container 30 to incline forward to send the essence into the sleeve piece 163. The outer perimeters of the first shell 141a and the second shell 141b are of an arc shape, with its inner diameter designed to match and fit the threads around the opening 31 of the essence container 30.

The ultrasonic vibration module 16 is disposed in the receiving room 111, and is provided with a atomized liquid outlet 1611 corresponding to shell hole 112, a connector hole 1411 of the first shell 141a, the absorbent 162 at the side of hollow slot 1631 of the sleeve piece 163, to connect to the power supply (not shown) through the power plug 20. When the switch 12 of the main body 10 is switched on, since the switch 12 is connected electrically to the electric circuit board 13, so the ultrasonic vibrator 161 of the ultrasonic vibration module 16 generates ultrasonic waves to vibrate and atomize the essence in the essence container 30, to spray it out of the atomized liquid outlet 1611.

The power plug 20 is pivotally disposed at the other end of the main body 10, and is connected electrically to the electric circuit board 13. On both sides of the power plug 20 are provided each with a rotation element 21. The rotation element 21 is provided with a pivot axis 211, corresponding to the pivot slot 17 of the main body 10. The pivot axis 211 penetrates though the pivot slot 17, such that the power plug 20 is able to rotate 180 degrees relative to the main body 10. The more than one ratchet 212 disposed by the pivot axis 211 corresponding to the more than one slot port 171, are able to position the power plug 20 relative to the main body 10. The power plug 20 is a Universal Series Bus (USB) plug (as shown in FIGS. 1, 2, 3, 4, 6, 7A, and 7B), a car charger connector (as shown in FIG. 5), or an ordinary plug (not shown). When the power plug 20 is inserted into the insertion slot of a power socket (not shown), the power plug 20 is able to rotate 180 degrees relative to the main body 10. Further, the main body 10 can be adjusted to a proper position, based on the positioning between the ratchet 212 nearby the pivot axis 211 and slot port 171, as such, positioning the atomized liquid outlet 1611 properly, and ready for turning on the switch 12 of the main body 10.

Figure 7A:
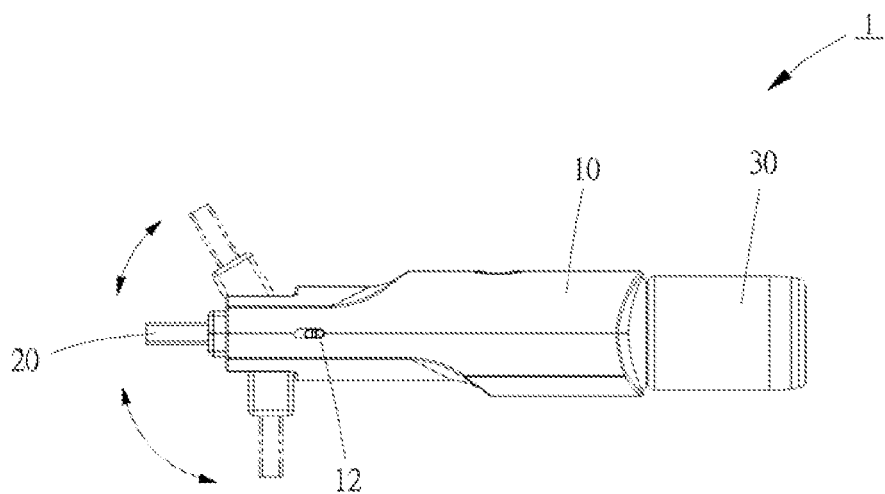
FIGS. 7A and 7B are the schematic diagrams of a rotable power plug of an essential oil diffuser according to an embodiment of the present invention.
Figure 7B:
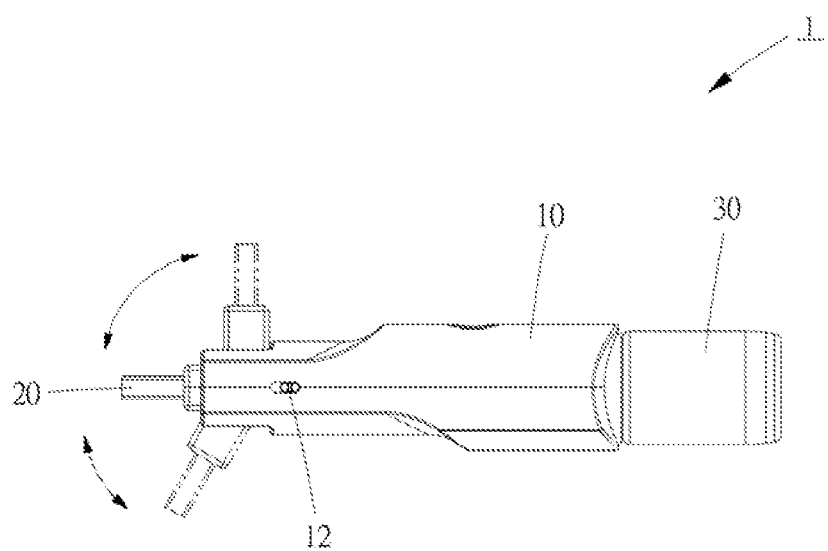

As shown in FIGS. 7A and 7B, when the power plug 20 is plugged to the power supply, the main body 10 can be rotated relative to the power plug 20 for 180 degrees. Based on the positioning of the slot port 171 nearby the pivot slot 17, and the ratchet 212 nearby the pivot axis 211, the main body 10 can be rotated to a proper degree. Then, after the essence in the essence container 30 is atomized, it is ejected and sprayed out of the essential oil diffuser 1 through the atomized liquid outlet 1611.

Subsequently, since the switch 12 is connected electrically to the electric circuit board 13, such that power is transmitted from the power plug 20 to the ultrasonic vibration module 16 via the electric circuit board 13, while the aroma rod 40 is inserted onto the essence container 30. Then, the essence container 30 is screwed into the connector shell 14 by fitting the first shell 141*a* and the second shell 141*b* together, while the cover 1632 of the sleeve piece 163 is used to cover the opening 31 of the essence container 30, to prevent the essence in the essence container 30 from pouring out of the opening 31. In this situation, the essence container 30 is inserted onto the first shell 141*a* and the second shell 141*b* of the connector shell 14, while the aroma rod 40 is inserted into the through hole 1633 of the sleeve piece 163. At this time, the ultrasonic vibration module 16 generates ultrasonic vibrations to vibrate and atomize the essence in the essence container 30, and eject and spray it out of the atomized liquid outlet 1611 of the essential oil diffuser 1. Namely, after the aroma rod 40 absorbs the essence from the essence container 30, the essence diffused is absorbed by the absorbent 162. Then, the ultrasonic vibrator 161 of the ultrasonic vibration module 16 generates vibrations to atomize the essence, to eject and spray the atomized essence out of the essential oil diffuser 1.

In contrast, when the switch 12 of the main body 10 is switched off, then power is cut off from the ultrasonic vibration module 16, the ultrasonic vibrator 161 is ceased from vibrating and atomizing the essential oil contained in the absorbent 162.

In applying the existing essential oil diffuser, for the essence container presently available on the market, its liquid essence must be reloaded into a specific container to be applicable, thus the essence container can not be used directly by the essential oil diffuser. However, in the present invention, the essence container 30 can be screwed into the connector shell 14 of the main body 10, so that the liquid essence in the essence container 30 can be used directly, without the need to purchase another essence container or perform reloading. Further, usually, the air molecules in the essence container 30 tend to act on and agitate the essence molecules to dissipate in the air and thus being volatile. Therefore, after the essence container 30 is screwed into the connector shell 14, the air molecules and essence molecules dissipated in the essence container 30 under the action of the ultrasonic vibration module 16, are vibrated and atomized, and will pass through the atomized liquid outlet 1611, to be ejected and sprayed out of the essential oil diffuser 1. Further, the aroma rod 40 presently available on the market can be inserted onto the essence container 30, to absorb the essence by means of siphon effect, thus it is full of essence and being volatile. Also, it can be inserted into the absorbent 162 and the sleeve piece 163, the connector hole 1411 of the first shell 141*a*, and the atomized liquid outlet 1611 of the ultrasonic vibration module 16, where the essence is volatile most. Therefore, when the ultrasonic vibration module 16 generates ultrasonic waves to act on the absorbent 162, it is able to atomize most of the air molecules and essence molecules in the essence container 30, and then eject and spray them out of the essential oil diffuser 1. The aroma rod 40 mentioned above is made of cotton rod or cotton strip, but the present invention is not limited to this.

The above detailed descriptions of the preferred embodiment are intended to describe more clearly the characteristics and spirit of the present invention. However, the preferred embodiments disclosed above are not intended to be any restrictions to the scope of the present invention. Conversely, its purpose is to include the various changes and equivalent arrangements which are within the scope of the appended claims.

What is claimed is:

1. An essential oil diffuser, comprising:
   a main body, including a shell, an electric circuit board, a connector shell, and an ultrasonic vibration module, wherein, a receiving room is formed in the shell, at one end of the shell is formed an opening, and on an upper end of the shell is formed a shell hole, the connector shell has a first shell and a second shell fitted together and is provided in the receiving room on a side of the shell opening, the connector shell is provided with a connector hole corresponding to the shell hole, the ultrasonic vibration module is disposed in the connector shell, the ultrasonic vibration module is provided with an atomized liquid outlet corresponding to the connector hole, and is connected to the connector shell, the ultrasonic vibration module includes at least an ultrasonic vibrator, and is sleeved in the connector shell by means of a sleeve piece, the electric circuit board is disposed in the receiving room of the shell, and is connected electrically to the ultrasonic vibrator;
   a power plug, pivotally disposed at another end of the main body, and is connected electrically to the electric circuit board, and
   an essence container screwed into the connector shell;

wherein the ultrasonic vibration module further includes an absorbent, the sleeve piece has a hollow slot, a cover is extended from the hollow slot along a direction substantially perpendicular to an axial direction of the hollow slot, a first through hole is formed inside the hollow slot and the absorbent is sleeved in the first through hole, wherein a second through hole is formed on the cover, an aroma rod is sleeved into the second through hole, so that the absorbent is disposed substantially perpendicular to the aroma rod.

2. The essential oil diffuser as claimed in claim 1, wherein the power plug is a Universal Serial Bus (USB) connector or a car charger connector.

3. The essential oil diffuser as claimed in claim 1, wherein a pivot slot is each provided in two inner sides at the other end of the main body, and a pivot axis is each provided on two outer sides of the power plug, while the pivot axis corresponds and passes through the pivot slot.

4. The essential oil diffuser as claimed in claim 3, wherein center of the absorbent is provided with an axial hole or a slot.

5. The essential oil diffuser as claimed in claim 3, wherein more than one ratchet are disposed nearby the pivot axis, while the shell is provided with more than one slot port corresponding to the ratchets.

6. The essential oil diffuser as claimed in claim 1, wherein the shell includes an upper shell and a lower shell.

7. The essential oil diffuser as claimed in claim 4, wherein the shell includes an upper shell and a lower shell.

* * * * *